United States Patent
Von Kleinsorgen

[11] Patent Number: 5,492,698
[45] Date of Patent: Feb. 20, 1996

[54] LANOLINE DERIVATIVES AS PENETRATION ENHANCING SUBSTANCES

[75] Inventor: Reinhard Von Kleinsorgen, Neuwied, Germany

[73] Assignee: LTS Lohmann Therapie-Systeme GmbH & Co. KG, Neuwied, Germany

[21] Appl. No.: 146,202

[22] PCT Filed: May 2, 1992

[86] PCT No.: PCT/EP92/00957

§ 371 Date: Nov. 12, 1993

§ 102(e) Date: Nov. 12, 1993

[87] PCT Pub. No.: WO92/20378

PCT Pub. Date: Nov. 26, 1992

[30] Foreign Application Priority Data

May 15, 1991 [DE] Germany ............ 41 15 849.0

[51] Int. Cl.⁶ .................................. A61F 13/00
[52] U.S. Cl. ............ 424/449; 514/946; 514/947
[58] Field of Search ............ 424/449; 514/946, 514/947

[56] References Cited

U.S. PATENT DOCUMENTS

| | | | |
|---|---|---|---|
| 3,472,931 | 10/1969 | Stoughton | 514/50 |
| 3,527,864 | 9/1970 | MacMillan et al. | 424/59 |
| 3,891,757 | 6/1975 | Higuchi | 424/310 |
| 3,896,238 | 7/1975 | Smith | 514/777 |
| 3,903,256 | 9/1975 | MacMillan et al. | 424/59 |
| 3,952,099 | 4/1976 | Smith | 514/152 |
| 4,046,886 | 9/1977 | Smith | 514/152 |
| 4,130,643 | 12/1978 | Smith | 514/171 |
| 4,130,667 | 12/1978 | Smith | 514/777 |
| 4,299,826 | 11/1981 | Luedders | 514/29 |
| 4,335,115 | 1/1982 | Thompson et al. | 514/29 |
| 4,343,798 | 8/1982 | Fawzi | 514/179 |
| 4,379,454 | 4/1983 | Campbell et al. | 424/448 |
| 4,405,616 | 9/1983 | Rajadhyaksha | 514/788 |
| 5,057,497 | 10/1991 | Calam et al. | 514/21 |

FOREIGN PATENT DOCUMENTS

| | | |
|---|---|---|
| 520987 | 3/1982 | Australia . |
| 189861 | 8/1986 | European Pat. Off. . |
| 370481 | 5/1990 | European Pat. Off. . |
| 2132130 | 11/1972 | France . |
| 2176105 | 6/1986 | United Kingdom . |
| WO87/00042 | 1/1987 | WIPO . |

OTHER PUBLICATIONS

Japanese Abstract JP61024517.
"Effect of Wool Waxes and Wool Wax Derivatives . . . ", El-Nimr et al., Fette–Seifen–Anstrichmittel, vol. 85 (1983), Aug., No. 8, Germany.

*Primary Examiner*—D. Gabrielle Phelan
*Attorney, Agent, or Firm*—Collard & Roe

[57] ABSTRACT

Formulation to increase the transdermal permeation of pharmaceutical substances or other biologically active substances, characterised by a content of a penetration enhancing portion of lanoline derivatives on their own or in a mixture with esters of isopropyl alcohol with long-chain fatty acids and/or polyethyleneglycol ethers of fatty alcohols with longer chains, as penetration enhancing substances, as well as a process for their production.

7 Claims, 1 Drawing Sheet

LANOLINE DERIVATIVES AS PENETRATION ENHANCING SUBSTANCES

The invention relates to lanoline derivatives on their own or in a mixture with polyethyleneglycol ethers of fatty alcohols with longer chains as penetration enhancing substances in formulations containing pharmaceutical substances or other biologically active substances.

Transdermal application offers a series of advantages for a multitude of pharmaceutical substances or other biologically active substances:

the skin is indefinitely accessible no change of medium occurs as in the case of oral application the operation is easy and convenient a single dosage suffices, rather than repeated daily doses positive psychological effects are registered a continuous long-time therapy is possible the therapy can be interrupted at any time a constant plasma level can be guaranteed for a prolonged period a plasma level which is too high initially, as is the case with intravenous application, is avoided, resulting in negligible secondary action the danger of an overdosage or underdosage is less a controlled release of active substances, particularly of those with a low therapeutic index, is guaranteed.

Some pharmaceutical substances which, owing to their high "first-pass" effect, their low dosage and their high effective potential, would otherwise be regarded as ideal, possess, in many cases, such a low skin permeation that it is not possible to obtain therapeutic plasma values. In the case of all these pharmaceutical substances it is necessary to add so-called penetration enhancers to the system. Along these lines a multiplicity of substances is described, listed in the following Patent Spefications:

U.S. Pat. No. 4,299,826, U.S. Pat. No. 4,343,798, U.S. Pat. No. 4,046,886, U.S. Pat. No. 4,130,643, U.S. Pat. No. 4,405,616, U.S. Pat. No. 4,335,115, U.S. Pat. No. 4,130,667, U.S. Pat. No. 3,903,256, U.S. Pat. No. 4,379,454, U.S. Pat. No. 3,527,864, U.S. Pat. No. 3,952 099, U.S. Pat. No. 3,896 238, U.S. Pat. No. 3 472 931.

In Addition to being able to fulfil their specific function, penetration enhancing substances must possess the following properties: even when they remain on the skin for a long time, at occlusive conditions, they must be tolerated by the skin, must not produce any allergies and must be compatible with the active substances involved.

The enhancers known from the literature can be assigned to various chemical classes:
1. Primary and secondary alcohols
   1.1 Short-chain primary alcohols $C_2$ to $C_8$
   1.2 Long-chain primary alcohols $C_4$ to $C_{16}$
   1.3 Secondary alcohols $C_3$ to $C_5$
2. Anionic tensides, such as, for example, Na-dodecylsulphate
3. Saturated and unsaturated fatty acids
4. Azones and derivatives (1-alkyl azacycloheptane-2-on, 1-alkyl azacycloalkanone)
5. Amides such as N,N-diethyl-3-methyl benzamide (DEET), N,N-diethyl-m-toluamide
6. Alkyl-N, N-dialkyl aminoacetate
7. Macrocyclic ketones and lactones
8. Pyrrolidones
9. Esters such as ethyl acetate, isopropyl myristate, glycerine monolaurate, diethyl sebacate, propylene glycol esters of saturated fatty acids
10. Terpenes such as limonene, menthol and cineole
11. Phosphatides
12. Organic acids, such as citric acid, salicylic acid, etc.
13. Cationic tensides or amines.

The existence of such a multitude of different substances of all possible chemical structures, all said to possess a penetration enhancing effect, makes a single working mechanism seem unlikely. Various thereof are, therefore, under discussion. mechanisms or combinations thereof are, therefore, under discussion.

1. The effect of solvents in relation to the active substance and skin lipides.
2. The effects on the lipide structure of the membrane.
3. The effects on the keratine and on the protein structure of the skin.

Bearing in mind both the multitude of interactions taking place within the skin and the varying chemical qualities manifested by the active substances concerned, the penetration enhancing properties of all these so-called enhancers in relation to one active substance can only be predicted with difficulty.

From previous experience it can be said that a penetration enhancing substance or a certain mixture only very rarely comply with the characteristics required by several pharmaceutical substances or pharmaceutical substance groups.

From JP-A-61024517 a transdermal therapeutic system for diseases of circulatory organs is known, comprising a plaster with an adhesive layer, a penetration enhancing substance, as well as a beta blocker as active substance. Isopropyl myristate and/or isopropyl lanolate are employed as penetration enhancers. The advantage of this system is said to be a long-lasting administration of the beta-blocking agent, without irritation of the skin occurring. The active substance reaches the blood circulation directly without passing the liver, which means that harmful side effects are avoided. For production of the system, the penetration enhancing substance is incorporated into the adhesive layer, which layer contains the beta blocker as active substance.

From FR-A-21 32 130 cosmetic formulation such as sun creams, facial, body or hand creams are known, in particular, as moisturizers. These are emulsions of the "water in oil" type. To stabilize these emulsions, mixtures of lanolates, such as magnesium lanolate, calcium, lithium, zink and aluminium lanolate are used. It is the object of the formulation to achieve improved hydration of the epidermis and improved protection thereof. According to example 1, one formulation, for example, contains magnesium lanolate, alcohol of lanoline, isopropyl palmitate, paraffine oil, almond oil, ozokerit, water and parahydroxybenzoate of methyl. The use of polyethyleneglycol ethers of fatty alcohols with longer chains as penetration enhancers in transdermal systems is mentioned, for example, in EP-A-0 189 861, page 10, lines 16 to 24. These penetration enhancers are, for instance, polyoxyethylenealkyl ethers selected from alkyl groups with 4 to 20, preferably 10 to 18, carbon atoms, with the addition of ethylene oxide, such as, for example, polyoxyethylene lauryl ether, polyoxyethylene cetyl ether, polyoxyether stearyl ether and polyoxyethylene oleyl ether. The use of substances in combination with lanoline derivates, however, is neither known from this document, nor does this document render the same obvious.

From WO/A/8700042 transdermal systems with isopropyl myristate as penetration enhancers for verapamile are known. Accordingly, in example 10 of this document, a comparatively good penetration of the active substance through the skin was observed by means of pre-treatment of the skin with isopropyl myristate prior to application of the matrix containing active substance. A comparison according to example 11 with isopropyl myristate incorporated into the matrix resulted in a penetration enhancing effect that was considerably lower. According to example 12, with the active substance verapamile a considerably increased permeation rate was obtained.

The object of the present invention is to supply penetration enhancing substances which are tolerated by the skin, are compatible with the active substance involved, do not produce allergies, which are, in addition, easily accessible and economical and, at the same time, possess a penetration enhancing effect on more than one active substance.

It has now been discovered, surprisingly, that certain lanoline derivatives have the property of increasing the penetration of certain pharmaceutical substances or active substances through the skin. These substances are normally employed in the cosmetic industry, to produce creams and lotions.

This object is solved, according to the invention, by employing lanoline derivatives together with polyethyleneglycol ethers of long-chain fatty alcohols as penetration enhancing substances in formulations containing pharmaceutical substances or other biologically active substances.

Preferred lanoline derivatives are selected from the group consisting of acetylated lanoline, acetylated lanoline alcohol, alcoxylated lanoline, lanoline acid, polyethoxylated lanoline acid, polyethoxylated lanoline alcohol, esters of lanoline acid with short-chain aliphatic alcohols such as isopropyl lanolate, polyethyleneglycol ethers of lanoline alcohol and esters of lanoline alcohol with long-chain fatty acids. In so far as polyethoxylated lanoline derivatives are used, the number of ethylene oxide molecules can lie between 2 and 50.

The linear or branched alcohols with $C_1$ to $C_4$ preferably primary or secondary ones, are suitable, above all, as esters of lanoline acid with short-chain aliphatic alcohols. Examples of these are methanol, ethanol, n-propanol, n-butanol, isopropanol. The saturated or unsaturated fatty acids, above all, such as lauric acid, palmitic acid and stearic acid are just as suitable as myristic acid, oleic acid and linoleic acid as esters of lanoline alcohol with long-chain fatty acids.

If esters of isopropanol with long-chain fatty acids and/or polyethyleneglycol ethers of fatty alcohols with longer chains are employed, as well, in combination with lanoline derivatives, then the foregoing fatty acids are suitable as fatty acid components of the corresponding isopropanol esters. The alcohols corresponding to the above-mentioned fatty acids, such as oleyl alcohol, lauryl alcohol, cetyl alcohol and stearyl alcohol, or their polyethyleneglycol ethers, which are obtained from the respective alcohols by means of reaction with differing molecular masses of ethylene oxide, are suitable as typical fatty alcohols with longer chains. Familiar products are the condensation products of oleyl alcohol with 2 to 50 moles of ethylene oxide, of lauryl alcohol with 2 to 40, cetyl alcohol with 2 to 45 and stearyl alcohol with 2 to 100 moles of ethylene oxide.

The penetration enhancing substance consists, preferably, of 1 to 100%-wt., above all of 1 to 60%-wt., of a lanoline derivative; and of 0 to 99, above all of 30 to 90%-wt, of a polyethyleneglycol ether of a fatty alcohol (the sum of the components being equal to 100).

A formulation for the administration of verapamile or lopamile through the skin is characterized in that for increasing the transdermal permeation lanoline derivatives are contained as a penetration enhancing portion, on their own or in a mixture with and/or polyethyleneglycol ethers of fatty alcohols with longer chains.

Provided the penetration enhancing substance is used in a therapeutic transdermal system (TTS), the latter consists of a backing layer impervious to active substances, and, adjacent to this, at least one reservoir containing active substances, in which the penetration enhancing portion is contained; a device for fixing the system to the skin; and, if necessary, a detachable protective release liner. The simplest case consists of a so-called single-layer formulation, in which the penetration enhancing substance (together with the active substance) is spread in a preferably self-adhesive matrix provided with a protective release liner which is dehesive on the side next to the skin and with a covering film on the side away from the skin.

In addition to a single-layer formulation of this sort, in which the penetration enhancer is incorporated in the preferably self-adhesive matrix from a solution or suspension, the pharmaceutical substance can also be triturated with the penetration enhancing substances, the mixture being applied on a substrate, preferably a piece of bonded fabric or woven fabric or foamed rubber. The substrate is then fixed to the skin by means of a self-adhesive film.

In addition to this, it is also possible to use a multilayered TTS. For example, in such a case the pharmaceutical substance can be placed on a substrate, either on its own or with part of the penetration enhancing substance, which substrate is placed on or in a first adhesive layer, seen from the skin, whereas either the total amount of the penetration enhancer, or at least a part thereof, is spread in a layer separated from the reservoir, preferably in the adhesive layer of the covering sheet. The penetration enhancing substances can, thus, be present in various layers in varying concentrations or amounts.

It has been shown that the substances used as penetration enhancers according to the invention can be used both together with the pharmaceutical substance in the usual matrix formulations with self-adhesive properties known to the person skilled in the art as well as jointly with the pharmaceutical or active substance in a gel, a cream or even an ointment fixed in the therapeutic system, and that these can be brought direct into contact with the intact skin.

Despite the application being repeated many times, no irritation of the skin could be determined.

The penetration enhancing effect is particularly advantageous with the active substances Verapamile and Gallopamile. A penetration enhancement of isopropyl myristate from PCT/WO87/00042 has been described for Verapamile. The lanoline derivatives used in accordance with the invention exhibit, however, a much more powerful penetration enhancing effect for Verapamile, as can be seen in the following examples.

Figure 1:
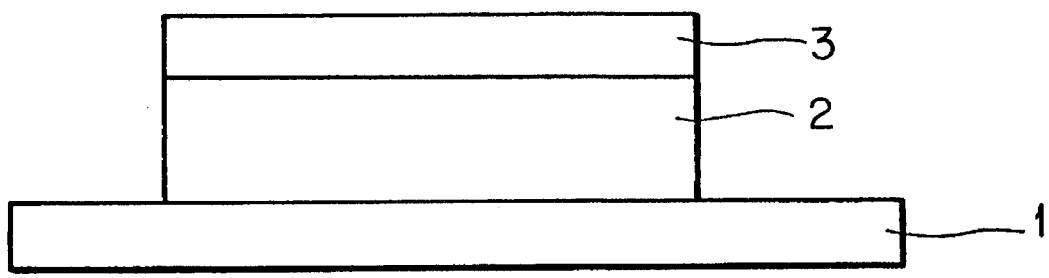
FIG. 1 represents a first embodiment of the invention.

The invention will be illustrated in detail by means of the following examples:

A. Single-layer Formulation

The formulations described as "single-layer formulation" refer to self-adhesive matrix formulations with the following TTS design (see figure):

The self-adhesive matrix (2) is placed on a dehesive protective layer (1), and covered by a covering sheet (3).

SINGLE-LAYER FORMULATION EXAMPLE 1

According to the present invention, a pharmaceutical product with a single-layer construction of the adhesive matrix containing the active substances, is produced as follows:

A pressure-sensitive adhesive mass containing the penetration enhancing components and the pharmaceutical substance, comprising:

0.170 kg polyisobutylene (with a mean molecular weight of 900,000 to 1,400,000)
0.202 kg of a solid aliphatic hydrocarbon resin (Trade name: Hercures C, molecular weight ca. 1100)
0.152 kg polyterpene resin
0.072 kg polymer of ethylene oxide $HO(CH_2—CH_2—O)nH$ n=200 (PEG 200)
0.072 kg colloidal silica
0.079 kg isopropyl lanolate
0.072 kg isopropyl myristate
0.181 kg Gallopamile
1.200 kg Special boiling point spirit 80-110 as solvent is applied in such a manner to a protective layer which has been aluminized on one side and made dehesive on both sides that an adhesive layer of 82 g/m² is obtained after the solvent has been volatilized.

After the adhesive layer has been covered by an impervious covering layer consisting of a polyester, the laminate obtained is divided up into individual parts in accordance with the therapeutic requirements.

RESULT EXAMPLE 1

Content: 14.80 mg/10 cm² of Gallopamile Penetration rate
(mouse skin): 9.61 mg of Gallopamile/10 cm²/24 h

SINGLE-LAYER FORMATION EXAMPLE 1

Production according to Example 1:
Composition:
0.213 kg polyisobutylene
0.253 kg hydrocarbon resin
0.190 kg polyterpene resin
0.045 kg PEG 200
0.091 kg Aerosile 200
0.050 kg isopropyl lanolate
0.045 kg isopropyl myristate
0.113 kg Verapamile
1.400 kg Special boiling point spirit 80-110
Adhesive layer after the solvent has been volatilized: 74 g/m²

RESULT EXAMPLE 1
Content: 8.4 mg Verapamile/10 cm²
Penetration Rate (mouse skin): 5.71 mg Verapamile/10 cm²/24 h

SINGLE-LAYER FORMULATION EXAMPLE 3

Production according to Example 1.
Composition:
0.213 kg polyisobutylene
0.253 kg hydrocarbon resin
0.190 kg polyterpene resin
0.045 kg PEG 200
0.091 kg Aerosile 200
0.050 kg isopropyl lanolate
0.045 kg polyoxyethylene (10) oleyl alcohol ether
0.113 kg Verapamile
1.300 kg Special boiling range spirit
Adhesive layer after the solvent has been volatilized: 85 g/m²

RESULT EXAMPLE 3

Content: 9.62 mg Verapamile/10 cm²
Penetration rate (mouse skin): 6.14 mg Verapamile/10 cm²/24 h

SINGLE-LAYER FORMULATION EXAMPLE 4

Preparation according to Example 1.
Composition:
0.223 kg polyisobutylene
0.265 kg hydrocarbon resin
0.199 kg polyterpene resin
0.047 kg PEG 200
0.095 kg Aerosile 200
0.050 kg isopropyl lanolate
0.119 kg Gallopamile
1.210 kg Special boiling range spirit 80–110
Adhesive layer after solvent has been volatilized: 75 g/m²

RESULT EXAMPLE 4

Content 8.89 mg Gallopamile/10 cm²
Penetration rate (mouse skin): 5.71 mg Gallopamile/10 cm²/24 h.

To produce further self-adhesive matrix formulations, the substances indicated in the table are mixed in the form of solutions or suspensions thereof (solvent or dispersion agent: petroleum spirit), applied to the protective layer which has been made dehesive by means of a coating device, freed of solvent by heating and lined with the covering sheet. The dry weight of the self-adhesive matrix (FG) is indicated in g/m² in the tabular outline (T means parts by weight).

The protective layer and the covering layer are the same as in Examples 1 to 4.

| | A. Single layer formulation | | | | | | | | | | | |
|---|---|---|---|---|---|---|---|---|---|---|---|---|
| No. | FG* (g/m²) | Poly-isobutelene | hydro-carbon resin | poly-terpene resin | PEG 200 | colloidal silica 200 | penetration enhancer | penetration enhancer | pharma-ceutic substance | content (mg/10 cm²) | release rate 24 h mg/10 cm² | mouse skin % |
| 1 | 95 | 23.5 T | 28.0 T | 21.0 T | 5.0 T | 10.0 T | — | — | A 12.5 T | 11.88 | 1.72 | 14.5 |
| 2 | 74 | 22.3 T | 26.5 T | 20.0 T | 4.8 T | 9.5 T | lanoline alcohol 5.0 T | — | A 11.9 T | 8.76 | 2.24 | 25.5 |
| 3 | 82 | 22.3 T | 26.5 T | 20.0 T | 4.8 T | 9.5 T | lanoline alcohol | — | A 11.9 T | 9.74 | 3.00 | 30.8 |

A. Single layer formulation

| No. | FG* (g/m²) | Poly-iso-butelene | hydro-carbon resin | poly-terpene resin | PEG 200 | colloidal silica 200 | penetration enhancer | penetration enhancer | pharma-ceutic substance | content (mg/10 cm²) | release rate 24 h mg/10 cm² | mouse skin % |
| --- | --- | --- | --- | --- | --- | --- | --- | --- | --- | --- | --- | --- |
| 4 | 79 | 22.3 T | 26.5 T | 20.0 T | 4.8 T | 9.5 T | 5.0 T 5.0 T acetylated lanoline alcohol | — | A 11.9 T | 9.38 | 2.73 | 29.1 |
| 5 | 72 | 22.3 T | 26.5 T | 20.0 T | 4.8 T | 9.5 T | isopropyl lanolate | — | A 11.9 T | 8.55 | 4.89 | 57.2 |
| 6 | 90 | 22.3 T | 26.5 T | 20.0 T | 4.8 T | 9.5 T | 5.0 T PPG-5-lanoline alcohol ether | — | B 11.9 T | 10.69 | 5.91 | 55.3 |
| 7 | 91 | 22.3 T | 26.5 T | 20.0 T | 4.8 T | 9.5 T | 5.0 T hydroxylated lanoline | — | A 11.9 T | 9.62 | 3.39 | 35.2 |
| 8 | 88 | 22.3 T | 26.5 T | 20.0 T | 4.8 T | 9.5 T | 5.0 T lanoline linoleate | — | A 11.9 T | 10.45 | 5.05 | 48.3 |
| 9 | 72 | 22.3 T | 26.5 T | 19.9 T | 4.7 T | 9.5 T | 5.0 T Isopropyl-lanolate | — | A 11.9 T | 8.53 | 4.18 | 49.0 |
| 10 | 166 | 22.3 T | 26.5 T | 19.9 T | 4.7 T | 9.5 T | 5.2 T isopropyl-myristate | — | A 11.9 T | 19.67 | 2.76 | 14.0 |
| 11 | 87 | 22.3 T | Abitol 26.5 T | 19.9 T | 4.5 T | 9.5 T | 5.2 T isopropyl-lanolate | — | B 11.9 T | 10.31 | 3.81 | 37.0 |
| 12 | 79 | 21.2 T | 25.2 T | 18.9 T | 4.5 T | 9.0 T | 5.2 T isopropyl-lanolate 5.9 T | — | A 11.3 T | 8.90 | 3.70 | 41.6 |

*FG: weight per unit area
A: verapamile base
B: gallopamile base
polyisobutelene
hydrocarbon resin
polyterpene resin
PEG 200
colloidal SiO$_2$ 200

B. Reservoir Formulation (Trituration)

The prescriptions dealt with in B.) refer in each case to the trituration of pharmaceutical substances with the penetration enhancing substances indicated in the table. In order to produce a TTS, these mixtures are applied to a substrate or carrier in the concentrations indicated in the table.

The substrate can consist of:

Woven fabric

Bonded fabric

Foam rubber (open-pored).

A sheet of woven fabric, bonded fabric or foam rubber which has been impregnated with the triturated mixture is fixed to the skin by means of a self-adhesive film.

EXAMPLE 13

130 mg of a mixture (trituration) consisting of:

2.0 g Verapamile 1.0 g isopropyl lanolate 1.0 g polyoxyethylene (10) oleyl alcohol ether 1.0 g isopropyl myristate are applied to a plaster consisting of a self-adhesive covering layer and a central piece of bonded fabric.

Penetration of the pharmaceutical substance through the mouse skin after application:

15.26 mg Verapamile/2.54 cm²/24 h

EXAMPLE 14

53 g of a mixture (trituration) consisting of:

2.0 g Verapamile 1.0 g isopropyl lanolate are applied to a plaster consisting of a self-adhesive covering layer and a central piece of bonded fabric.

Penetration of the pharmaceutical substance through the mouse skin after application:

6.76 mg Verapamile/2.54 cm²/24 h.

B. Reservoir formulation (trituration)

| No. | drug (g) | penetration enhancer (g) | penetration enhancer (g) | penetration enhancer (g) | miscellaneous | trituration amount applied mg/2.54 cm² | drug content mg/2.54 cm² | release 24 h mg/2.54 cm² | mouse skin % |
| --- | --- | --- | --- | --- | --- | --- | --- | --- | --- |
| 15 | 2.5 | — | PEG 200 | — | colloidal | 94 | A 31.8 | 0.53 | 1.7 |

-continued

| | | | B. Reservoir formulation (trituration) | | | | | | |
|---|---|---|---|---|---|---|---|---|---|
| No. | drug (g) | penetration enhancer (g) | penetration enhancer (g) | penetration enhancer (g) | miscellaneous | trituration amount applied mg/2.54 cm² | drug content mg/2.54 cm² | release 24 h mg/2.54 cm² | mouse skin % |
| 16 | 2.0 | isopropyl lanolate 1.0 | 4.0 PEG 200 4.0 | 1.0 | silica 0.9 — | 260 | A 104.0 | 2.88 | 2.8 |

C. Multilayered Formulation

Figure 2:
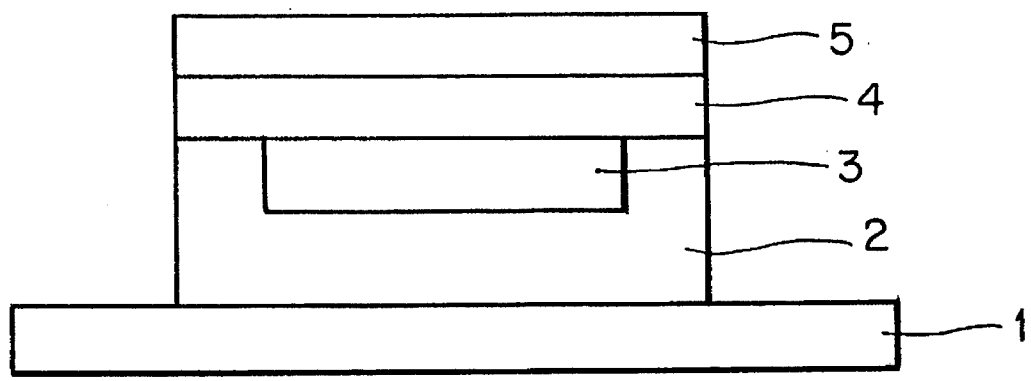
FIG. 2 represents a second embodiment of the invention.

The multilayered formulations described below exhibit the following construction (see FIG. 2):

An adhesive layer (2) is arranged on a dehesively finished protective layer (1) on or in which the reservoir (3) is arranged. The reservoir (3) comprises an adhesive sheet, impregnated with both the pharmaceutical substance and a polyethyleneglycol ether of oleyl alcohol. The reservoir (3) is backed with a covering layer (5) which is coated with adhesive (4).

To produce such a system, one proceeds as follows:

The dehesively finished protective layer (1) coated with the adhesive (2) is provided with a sheet of bonded fabric (3). This sheet of bonded fabric is doped with the active substance formulation. Subsequently, the covering layer (5), coated with adhesive is laminated thereon.

EXAMPLE 18

Production:

A release liner which has been aluminized on one side and rendered dehesive on both sides is coated with a mixture consisting of:

72.1 g polyacrylate adhesive solution 32.2 g polyacrylate basic 6.7 g isopropyl lanolate in such a manner that once the solvent has been volatilized, a weight per area of 50 g/m² of adhesive layer results (adhesive 2 matrix).

A sheet of bonded fabric which is doped with a mixture consisting of equal parts of Verapamile and polyoxyethylene (10) oleyl alcohol ether is laid on this adhesive layer.

Concentration of Verapamile in the bonded fabric after doping: 65.3 mg/13.85 cm²

The doped bonded fabric and the coated protective layer are covered (laminated) with a pressure-sensitive backing sheet consisting of a polyacrylate matrix with a weight per area of 100 g/m² and a polyester sheet in such a manner that the doped bonded fabric is encompassed by the two self-adhesive matrices. The laminate obtained is stamped in such a way that a 1 cm wide adhesive margin free of active substances is left next to the bonded fabric.

Mouse skin penetration: 3.78 mg Verapamile/2,54 cm²/24 h

I claim:

1. Formulation to increase the transdermal permeation of pharmaceutical substances or other biologically active substances, consisting essentially of a content of a penetration enhancing portion of lanolin derivatives alone or together with polyethylene glycol ethers of fatty alcohols as penetration enhancing substances, whereby the lanolin derivatives are selected from the group consisting of acetylated lanolin, acetylated lanolin alcohol, alkoxylated lanolin, lanolin acid, polyethoxylated lanolin acid, polyethoxylated lanolin alcohol, esters of lanolin acid with aliphatic alcohols, isopropyl lanolate and esters of lanolin alcohol with fatty acids.

2. Formulation according to claim 1, wherein the polyethyleneglycol ethers of fatty alcohols are selected from the group consisting of reaction products of oleyl alcohol with 2–50 moles of ethylene oxide, lauryl alcohol with 2–40 moles of ethylene oxide, cetyl alcohol with 2–45 moles of ethylene oxide and stearyl alcohol with 2–100 moles of ethylene oxide.

3. Formulation according to claim 1, wherein the penetration enhancing substance consists essentially of 1 to 100%-wt. of a lanoline derivative, and of 0 to 99%-wt. of a polyethyleneglycol ether of fatty alcohols, the sum of the components always amounting to 100%wt.

4. Formulation for the administration through the skin consisting essentially of verapamile or gallopamile and for increasing the transdermal permeation lanolin derivatives, on their own or in a mixture with polyethyleneglycol ethers of fatty alcohols are contained therein as a penetration enhancing portion; and whereby the lanolin derivates are selected from the group consisting of acetylated lanolin, acetylated lanolin alcohol, alkoxylated lanolin, lanolin acid, polyethoxylated lanolin acid, polyethoxylated lanolin alcohols, esters of lanolin acid with aliphatic alcohols, isopropyl lanolate and esters of lanolin alcohol with fatty acids.

5. Formulation according to claim 4, wherein said lanolin derivatives, are selected from the group consisting of acetylated lanolin, acetylated lanolin alcohol, alkoxylated lanolin, lanolin acid, polyethoxylated lanolin acid, polyethoxylated lanolin alcohol, esters of lanolin acid with aliphatic alcohols, and esters of lanolin alcohols with fatty acids alone or in a mixture with esters of isopropyl alcohols with fatty acids selected from the group consisting of isopropyl isostearate, isopropyl laurate, isopropyl linoleate, isopropyl myristate, isopropyl palmitate and isopropyl stearate with polyethylene glycol ethers of fatty alcohols selected from the group consisting of reaction products of oleyl alcohol with 2 to 50 moles ethylene oxide, lauryl alcohol with 2 to 40 moles ethylene oxide, cetyl alcohol with 2 to 45 moles ethylene oxide and stearyl alcohol with 2 to 100 moles ethylene oxide as penetration enhancing substances for formulations containing verapamile or gallopamile.

6. Formulation according to claim 1, consisting essentially of a transdermal therapeutic system.

7. Formulation according to claim 3, wherein the penetration enhancing substance consists essentially of 1 to 60%-wt. of a lanolin derivative, and 30 to 90%-wt. of a polyethyleneglycol ether of fatty alcohols, the sum of the components always amounting to 100% wt.

* * * * *